US012423512B2

(12) United States Patent
Zimmerman et al.

(10) Patent No.: US 12,423,512 B2
(45) Date of Patent: *Sep. 23, 2025

(54) INSERTION OF STANDARD TEXT IN TRANSCRIPTION

(71) Applicant: DeliverHealth Solutions LLC, Madison, WI (US)

(72) Inventors: Roger S. Zimmerman, Wellesley, MA (US); Paul Egerman, Weston, MA (US); Robert G. Titemore, Lexington, MA (US); George Zavaliagkos, Acton, MA (US)

(73) Assignee: Deliver Health Solutions LLC, Madison, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 18/107,664

(22) Filed: Feb. 9, 2023

(65) Prior Publication Data
US 2023/0281382 A1    Sep. 7, 2023

Related U.S. Application Data

(60) Continuation of application No. 16/581,149, filed on Sep. 24, 2019, now Pat. No. 11,586,808, which is a division of application No. 13/584,052, filed on Aug. 13, 2012, now Pat. No. 10,423,721, which is a division of application No. 11/478,711, filed on Jun. 29, 2006, now Pat. No. 8,286,071.

(51) Int. Cl.
G06F 40/186    (2020.01)
G06F 40/274    (2020.01)
G16H 10/60     (2018.01)

(52) U.S. Cl.
CPC ......... *G06F 40/186* (2020.01); *G06F 40/274* (2020.01); *G16H 10/60* (2018.01)

(58) Field of Classification Search
None
See application file for complete search history.

(56) References Cited

U.S. PATENT DOCUMENTS 5,051,924 A    9/1991    Bergeron et al.
5,146,439 A    9/1992    Jackmann et al.
(Continued)

OTHER PUBLICATIONS

Batty et al., "The development of a portable real-time display of voice source characteristics", IEEE 2:419-422 (2000).
(Continued)

*Primary Examiner* — Maikhanh Nguyen
(74) *Attorney, Agent, or Firm* — Andrew J. Tibbetts; Greenberg Traurig, LLP

(57) ABSTRACT

A computer program product, for automatically editing a medical record transcription, resides on a computer-readable medium and includes computer-readable instructions for causing a computer to obtain a first medical transcription of a dictation, the dictation being from medical personnel and concerning a patient, analyze the first medical transcription for presence of a first trigger phrase associated with a first standard text block, determine that the first trigger phrase is present in the first medical transcription if an actual phrase in the first medical transcription corresponds with the first trigger phrase, and insert the first standard text block into the first medical transcription.

16 Claims, 13 Drawing Sheets

(56) References Cited

U.S. PATENT DOCUMENTS

| | | |
|---|---|---|
| 5,148,366 A | 9/1992 | Buchanan et al. |
| 5,179,627 A * | 1/1993 | Sweet .................. H04M 11/10 704/200 |
| 5,465,378 A | 11/1995 | Duensing et al. |
| 5,519,808 A | 5/1996 | Benton, Jr. et al. |
| 5,602,982 A | 2/1997 | Judd et al. |
| 5,617,855 A | 4/1997 | Waletzky et al. |
| 5,748,888 A | 5/1998 | Angelo et al. |
| 5,781,891 A | 7/1998 | Dvorak et al. |
| 5,799,279 A | 8/1998 | Gould et al. |
| 5,812,882 A | 9/1998 | Raji et al. |
| 5,845,253 A | 12/1998 | Rensimer et al. |
| 5,857,212 A | 1/1999 | Van De Vanter |
| 5,875,448 A | 2/1999 | Boys et al. |
| 5,930,759 A | 7/1999 | Moore et al. |
| 5,970,448 A | 10/1999 | Goldhor et al. |
| 5,974,124 A | 10/1999 | Schlueter, Jr. et al. |
| 6,014,626 A | 1/2000 | Cohen |
| 6,026,363 A | 2/2000 | Shepard |
| 6,029,124 A | 2/2000 | Gillick et al. |
| 6,082,776 A | 7/2000 | Feinberg |
| 6,122,614 A * | 9/2000 | Kahn .................. G10L 15/063 704/270 |
| 6,154,726 A | 11/2000 | Rensimer et al. |
| 6,175,822 B1 * | 1/2001 | Jones .................. H04L 65/613 369/29.01 |
| 6,208,964 B1 | 3/2001 | Sabourin |
| 6,219,644 B1 | 4/2001 | VanBuskirk |
| 6,292,771 B1 | 9/2001 | Haug et al. |
| 6,348,545 B2 | 2/2002 | Inagaki et al. |
| 6,366,882 B1 | 4/2002 | Bijl et al. |
| 6,374,225 B1 | 4/2002 | Hejna, Jr. |
| 6,415,256 B1 | 7/2002 | Ditzik |
| 6,438,545 B1 | 8/2002 | Beauregard et al. |
| 6,697,841 B1 * | 2/2004 | Sheffield .................. H04L 51/216 704/201 |
| 6,738,784 B1 * | 5/2004 | Howes .................. H04L 67/06 704/235 |
| 6,766,297 B1 | 7/2004 | Lamer et al. |
| 6,789,060 B1 * | 9/2004 | Wolfe .................. G06F 40/186 704/235 |
| 6,813,603 B1 | 11/2004 | Groner et al. |
| 6,834,264 B2 | 12/2004 | Lucas et al. |
| 6,839,669 B1 | 1/2005 | Gould et al. |
| 6,865,258 B1 | 3/2005 | Polcyn |
| 6,915,254 B1 | 7/2005 | Heinze et al. |
| 6,950,994 B2 | 9/2005 | Dharap |
| 6,961,699 B1 | 11/2005 | Kahn et al. |
| 6,980,953 B1 | 12/2005 | Kanevsky et al. |
| 6,996,445 B1 | 2/2006 | Kamijo |
| 7,016,844 B2 * | 3/2006 | Othmer .................. H04L 67/12 704/E15.047 |
| 7,035,804 B2 | 4/2006 | Saindon et al. |
| 7,236,931 B2 | 6/2007 | Chuang et al. |
| 7,236,932 B1 | 6/2007 | Grajski |
| 7,274,775 B1 | 9/2007 | Zavaliagkos et al. |
| 7,292,975 B2 | 11/2007 | Lovance et al. |
| 7,539,619 B1 | 5/2009 | Seligman et al. |
| 7,613,610 B1 | 11/2009 | Zimmerman et al. |
| 7,650,628 B2 | 1/2010 | Zimmerman et al. |
| 7,668,718 B2 | 2/2010 | Kahn et al. |
| 7,774,694 B2 * | 8/2010 | Watson .................. G10L 15/26 715/224 |
| 7,831,423 B2 | 11/2010 | Schubert |
| 7,836,412 B1 | 11/2010 | Zimmerman |
| 7,860,717 B2 | 12/2010 | Urhbach et al. |
| 7,958,443 B2 | 6/2011 | Rosen et al. |
| 8,032,372 B1 | 10/2011 | Zimmerman et al. |
| 8,145,644 B2 | 3/2012 | Faulkner et al. |
| 8,286,071 B1 | 10/2012 | Zimmerman et al. |
| 10,423,721 B2 | 9/2019 | Zimmerman et al. |
| 2001/0033639 A1 | 10/2001 | Martin |
| 2002/0013709 A1 | 1/2002 | Ortega et al. |
| 2002/0055788 A1 * | 5/2002 | Petrie .................. H04L 69/329 700/2 |
| 2002/0065653 A1 | 5/2002 | Kriechbaum et al. |
| 2002/0095290 A1 | 7/2002 | Kahn et al. |
| 2002/0099717 A1 | 7/2002 | Bennett |
| 2002/0188452 A1 | 12/2002 | Howes |
| 2003/0046080 A1 | 3/2003 | Hejna, Jr. |
| 2003/0046350 A1 | 3/2003 | Chintalapati et al. |
| 2003/0050777 A1 | 3/2003 | Walker, Jr. |
| 2003/0067495 A1 | 4/2003 | Pu et al. |
| 2003/0083885 A1 | 5/2003 | Frimpong-Ansah |
| 2003/0097253 A1 | 5/2003 | Hoi |
| 2003/0105631 A1 | 6/2003 | Habte |
| 2003/0115057 A1 | 6/2003 | Junqua et al. |
| 2003/0115083 A1 | 6/2003 | Masarie, Jr. |
| 2003/0144885 A1 | 7/2003 | Sachdev |
| 2004/0030704 A1 * | 2/2004 | Stefanchik .................. G16H 50/70 |
| 2004/0049385 A1 | 3/2004 | Lovance et al. |
| 2004/0064317 A1 * | 4/2004 | Othmer .................. H04L 67/306 704/E15.047 |
| 2004/0111265 A1 | 6/2004 | Forbes et al. |
| 2004/0172245 A1 | 9/2004 | Rosen et al. |
| 2004/0193049 A1 | 9/2004 | Greenberg |
| 2004/0204938 A1 | 10/2004 | Wolfe et al. |
| 2004/0243545 A1 | 12/2004 | Boone et al. |
| 2004/0243551 A1 | 12/2004 | Boone et al. |
| 2005/0071196 A1 | 3/2005 | Del Pin |
| 2005/0096910 A1 | 5/2005 | Watson et al. |
| 2005/0102140 A1 * | 5/2005 | Davne .................. G16H 40/67 704/235 |
| 2005/0114122 A1 | 5/2005 | Uhrbach et al. |
| 2005/0114129 A1 * | 5/2005 | Watson .................. G10L 15/26 704/235 |
| 2005/0149747 A1 | 7/2005 | Wesinger, Jr. et al. |
| 2005/0171762 A1 | 8/2005 | Ryan et al. |
| 2005/0187766 A1 | 8/2005 | Rennillo et al. |
| 2006/0031096 A1 | 2/2006 | Buttner et al. |
| 2006/0041427 A1 | 2/2006 | Yegnanarayanan et al. |
| 2006/0074656 A1 | 4/2006 | Mathias et al. |
| 2006/0089857 A1 | 4/2006 | Zimmerman et al. |
| 2006/0149558 A1 | 7/2006 | Kahn et al. |
| 2006/0190249 A1 | 8/2006 | Kahn et al. |
| 2006/0193450 A1 | 8/2006 | Flynt et al. |
| 2006/0206943 A1 | 9/2006 | Ellison et al. |
| 2006/0253895 A1 | 11/2006 | Brandofino et al. |
| 2006/0272025 A1 | 11/2006 | Mononen |
| 2007/0011608 A1 | 1/2007 | Titemore et al. |
| 2007/0143857 A1 | 6/2007 | Ansari |
| 2007/0156400 A1 | 7/2007 | Wheeler |
| 2007/0203901 A1 | 8/2007 | Prado et al. |
| 2007/0276649 A1 | 11/2007 | Schubert |
| 2007/0283444 A1 | 12/2007 | Jang |
| 2007/0294745 A1 | 12/2007 | Tan et al. |
| 2007/0300287 A1 | 12/2007 | Wynne et al. |
| 2012/0310644 A1 | 12/2012 | Zimmerman et al. |

OTHER PUBLICATIONS

Grasso, "Automated speech recognition in medical applications" pp. 1-8 (1995).

Rosenthal et al., "Computer-based speech recognition as a replacement for medical transcription" pp. 23-25 (Dec. 1996).

Sistrom et al., Managing Predefined Templated and Macros for a Departmental Speech Recognition System Using Common Software. Journal of Digital Imaging. 2001;14(3): 131-41.

* cited by examiner

80

Please specify the Standard Text and Triggers:

1) You must enter either a speaker or worktype, or both:

SPEAKER: ▓▓▓▓▓▓▓▓▓▓▓▓▓▓▓ ~ 82

WORKTYPE: ▓▓▓▓▓▓▓▓▓▓▓▓▓▓▓ ~ 84

2) You must enter the standard text or provide a file name which contains it:

Text:                                    Browse for Filename
                                                        90
                                    86

3) Enter a description of the standard:

_____  87
_____

4) You must provide one or more verbal triggers:

trigger 1: _____ 88 trigger 2: _____ 88 trigger 3: _____ 88 trigger 4: _____ 88

SUBMIT  92

FIGURE 3

| Index | Trigger | Standard Text File | Description |
|---|---|---|---|
| 1 | [Please] (use/insert) my normal (PE/exam) | C:/standards/PE1.txt | Normal physical examination summary |
| 2 | Normal Chest [xray] | C:/standards/Johnson-chest.doc | Normal chest x-ray summary |
| 3 | Insert high blood pressure physical exam macro | C:/standards/generated035.txt | Normal physical examination, except high blood pressure, summary |
| 4 | Use P.E. Template | PE_with_blanks.doc | Physical examination template with blanks |
| ... | ... | ... | ... |

FIGURE 4A

| Speaker ID | Worktype | Standards |
|---|---|---|
| 1237 | Office Note | 1, 4, 12 ← 104 |
| 1237 | Consultation | 236, 418 |
| 890 | Office Note | 1, 3, 18 |
| 890 | Radiology | 2, 77 |
| 618 | Radiology | 2, 99 |
| ... | ... | ... |

| Line | ASR | Formatted |
|---|---|---|
| 1 | THIS | <null> |
| 2 | IS | <null> |
| 3 | DOCTOR | <null> |
| 4 | JONES | <null> |
| 5 | ON | <null> |
| 6 | JANE | <null> |
| 7 | SMYTHE | <null> |
| 8 | <null> | HISTORY |
| 9 | <null> | OF |
| 10 | <null> | PRESENT |
| 11 | <null> | ILLNESS: |
| 12 | <null> | The |
| 13 | PATIENT | patient |
| 14 | IS | is |
| 15 | A | a |
| 16 | FIFTY | <null> |
| 17 | THREE | <null> |
| 18 | YEAR | <null> |
| 19 | OLD | 53-year-old |
| 20 | FEMALE | female |
| 21 | <null> | who |
| 22 | COMES | comes |
| 23 | TO | into |
| 24 | THE | the |
| 25 | CLINIC | clinic |
| 26 | FOR | for |
| 27 | HER | her |
| 28 | ANNUAL | annual |
| 29 | CHECKUP. | checkup. |
| 30 | USE | PHYSICAL |
| 31 | MY | <null> |
| 32 | NORMAL | <null> |
| 33 | EXAM | EXAMINATION: |
| 34 | <null> | GENERAL: |
| 35 | <null> | Appears |
| 36 | <null> | well-developed, |
| 37 | <null> | well-nourished, |
| 38 | <null> | in |
| 39 | <null> | no |
| 40 | <null> | acute |
| 41 | <null> | distress. |
| 42 | <null> | Normal |
| 43 | TEMPLATE | temperature, |

↑ 142   ↑ 144

| Line | ASR | Formatted |
|---|---|---|
| 44 | <null> | pulse |
| 45 | <null> | and |
| 46 | <null> | BP |
| 47 | <null> | as |
| 48 | <null> | indicated |
| 49 | <null> | in |
| 50 | <null> | chart. |
| 51 | HERE. | HEENT: |
| 52 | <null> | Normal, |
| 53 | <null> | anicteric |
| 54 | <null> | PERRLA, |
| 55 | <null> | EMOI. |
| 56 | <null> | Nerologic: |
| 57 | <null> | A&O |
| 58 | <null> | x3. |
| 59 | <null> | Neck: |
| 60 | <null> | Supple, |
| 61 | <null> | No |
| 62 | <null> | JVD. |
| 63 | .... | |
| 64 | <null> | Gait |
| 65 | <null> | is |
| 66 | <null> | normal. |
| 67 | ALLERGIC | ALLERGIES: |
| 68 | TO | No |
| 69 | NKDA | known |
| 70 | <null> | drug |
| 71 | <null> | allergies. |
| 72 | MEDS. | MEDICATIONS: |
| 73 | ZESTRIL | Zestril |
| 74 | TEN | 10 |
| 75 | MILLIGRAMS | mg, |
| 76 | BABY | baby |
| 77 | ASPIRIN | aspirin, |
| 78 | Q.D. | daily. |

Updating Standard Text Blocks

Please specify the Speaker and Work Type:

1) SPEAKER: _____  182

2) WORKTYPE: _____  184

186
SUBMIT

FIGURE 10

Updating Standard Text Blocks

For: Dr. I. M. Jones, physical examination

Please select and update the desired Standard Text:

1) Choose the standard text for updating.

| Current File | Standard Text File | Description |
|---|---|---|
| X | C:/standards/PE1.txt | Normal physical examination summary |
| | C:/standards/Johnson-chest.doc | Normal chest x-ray summary |
| | C:/standards/generated035.txt | Normal physical examination, except high blood pressure, summary |
| | PE_with_blanks.doc | Physical examination template with blanks |

2) You may update/edit the standard text of the file selected in 1) above.

Text:

PHYSICAL EXAMINATION:
    GENERAL: Appears well-developed, well-nourished, in no acute distress.
        Normal temperature, pulse and BP as indicated in chart.
    HEENT: Normal, anicteric PERRLA, EMOI.
    NEUROLOGIC: A&O x3.
    NECK: Supple, no JVD.
    Gait is normal.

[SUBMIT]

FIGURE 11

INSERTION OF STANDARD TEXT IN TRANSCRIPTION

CROSS-REFERENCE TO RELATED APPLICATIONS

This application claims the benefit under 35 U.S.C. § 120 as a continuation of U.S. application Ser. No. 16/581,149, filed Sep. 24, 2019, entitled "INSERTION OF STANDARD TEXT IN TRANSCRIPTION," now U.S. Pat. No. 11,586,808, which claims the benefit under 35 U.S.C. § 120 as a divisional of U.S. application Ser. No. 13/584,052, filed Aug. 13, 2012, entitled "INSERTION OF STANDARD TEXT IN TRANSCRIPTION," now U.S. Pat. No. 10,423,721, which claims the benefit under 35 U.S.C. § 120 as a divisional of U.S. application Ser. No. 11/478,711, filed Jun. 29, 2006, entitled "INSERTION OF STANDARD TEXT IN TRANSCRIPTION," now U.S. Pat. No. 8,286,071.

BACKGROUND OF THE INVENTION

Healthcare costs in the United States account for a significant share of the GNP. The affordability of healthcare is of great concern to many Americans. Technological innovations offer an important leverage to reduce healthcare costs.

Many Healthcare institutions require doctors to keep accurate and detailed records concerning diagnosis and treatment of patients. Motivation for keeping such records include government regulations (such as Medicare and Medicaid regulations), desire for the best outcome for the patient, and mitigation of liability. The records include patient notes that reflect information that a doctor or other person adds to a patient record after a given diagnosis, patient interaction, lab test or the like.

Record keeping can be a time-consuming task, and the physician's time is valuable. The time required for a physician to hand-write or type patient notes can represent a significant expense. Verbal dictation of patient notes offers significant time-savings to physicians, and is becoming increasingly prevalent in modern healthcare organizations.

Over time, a significant industry has evolved around the transcription of medical dictation. Several companies produce special-purpose voice mailbox systems for storing medical dictation. These centralized systems hold voice mailboxes for a large number of physicians, each of whom can access a voice mailbox by dialing a phone number and putting in his or her identification code. These dictation voice mailbox systems are typically purchased or shared by healthcare institutions. Prices can be over $100,000 per voice mailbox system. Even at these prices, these centralized systems save healthcare institutions vast sums of money over the cost of maintaining records in a more distributed fashion.

Using today's voice mailbox medical dictation systems, when a doctor completes an interaction with a patient, the doctor calls a dictation voice mailbox, and dictates the records of the interaction with the patient. The voice mailbox is later accessed by a medical transcriptionist who listens to the audio and transcribes the audio into a text record.

The medical transcriptionist's time is less costly for the hospital than the doctor's time, and the medical transcriptionist is typically much more familiar with the computerized record-keeping systems than the doctor is, so this system offers a significant overall cost saving to the hospital.

To reduce costs further, health care organizations have deployed speech recognition technology. Some efforts have been made to utilize speech recognition technology for the purpose of producing written documents. Such efforts have met with limited success, however, since producing a literal transcription of a dictation has not resulted in a document sufficiently close to the desired final document.

Until recently, most deployed automatic speech recognition systems were front-end or real-time systems. In these applications, the speaker interacts directly with the speech recognition device, which hypothesizes the spoken words and outputs them to the computer terminal with a short delay. The speaker may then be required to correct the output, either using voice commands or by typing.

In an application of background speech recognition to medical transcription, the automatic speech recognition ("ASR") process is run "off line", without real-time clinician interaction. The speaker dictates normally, and the speech recognition process is run in batch mode at a later time. Draft transcriptions produced by the ASR process may then be edited by the clinician or by a Medical Transcriptionist ("MT") before being added to the medical record. An example of this type of ASR application is the EditScript product from eScription.

In background speech recognition, the speaker does not have access to the text as s/he dictates. As such, the speaker cannot interact with the speech recognition device in order to improve the appearance of the document. Moreover, the use of such verbal directives is counter-productive to the efficiency of the dictation process. Health care clinicians are used to simply dictating the medical information in the way that they feel comfortable and assuming that the final documented will be formatted according to generally accepted standards.

A hybrid of the front-end and background speech recognition process is also possible. In these "near real-time" applications, the speaker dictates for some period of time, before indicating to the speech-recognition device that the dictation has been completed. At this point, the speech-recognition device completes its processing on all of the audio received and outputs the entire transcription to the computer terminal for editing, either with voice or typing, by the user. In general, front-end speech recognition software is resident on the computer at which the speaker is speaking, whereas background speech-recognition runs on a high-end server, which is often remote from the dictation device. Near-real-time speech recognition may be run in either of these modes, or in a combination scenario, where some of the speech-recognition processing is done on the speaker's computer, and some is done on a remote high-end server.

Often, health care clinicians perform procedures and examinations which are similar to those they have performed previously. For example, a Urologist may perform several routine vasectomies each day, or a Radiologist may examine dozens of normal chest x-rays during a shift. In cases such as this, the medical record for the incidence of service is nearly, if not completely, identical to the document for all other such services. Accordingly, clinicians often dictate words to the effect that a certain "standard" document should be inserted as the transcription for the dictation. Sometimes, this standard document is the entire desired transcription. For example, a Urologist may say: "Please use my normal vasectomy template," indicating that the entire standard vasectomy description should be inserted as the transcription. In other circumstances, the standard text may comprise a subset of the desired final transcription, in which case the clinician will continue with the remainder of the dictation in the usual fashion. Clinicians may dictate several such standard sub-sections within the course of a dictation and may also include standard dictation. The MT analyzes the dictation to determine whether standard text (at least for that speaker) can be inserted, and obtains and inserts the standard text as appropriate.

In these circumstances, the medical transcriptionist may have access to the text that is indicated by the dictation. In general, the MT will use the transcription device to access a list or menu of files, each file representing standard text. The appropriate file is then selected, and the standard text inserted into the transcription document. Selection and insertion of standard texts into transcription documents requires experience and, depending on how large the list of potential files, can be very time-consuming. In addition, managing standard documents is challenging for health-care institutions, particularly when MTs are dispersed geographically and their access to the transcription system is not synchronous with changes to the documents. If the MT does not have access to the most recent version of a standard document, the transcription may need to be reviewed and edited by a transcription supervisor. This workflow is especially costly.

SUMMARY OF THE INVENTION

Embodiments of the invention are directed to the use of speech recognition to insert standard text into medical transcriptions as well as the system workflow needed to support this behavior.

In general, in an aspect, the invention provides a computer program product for automatically editing a medical record transcription, the computer program product residing on a computer-readable medium and including computer-readable instructions for causing a computer to: obtain a first medical transcription of a dictation, the dictation being from medical personnel and concerning a patient; analyze the first medical transcription for presence of a first trigger phrase associated with a first standard text block; determine that the first trigger phrase is present in the first medical transcription if an actual phrase in the first medical transcription corresponds with the first trigger phrase; and insert the first standard text block into the first medical transcription.

Implementations of the invention may include one or more of the following features. The computer program product further includes instructions for causing the computer to insert text from the first transcription of the dictation proximate to the actual phrase corresponding to the first trigger phrase into the first standard text block. The instructions for causing the computer to insert text are configured to cause the computer to replace at least a portion of the first standard text block with the text proximate to the actual phrase corresponding to the first trigger phrase. The instructions for causing the computer to insert text are configured to cause the computer to fill a placeholder portion of the first standard text block with the text proximate to the actual phrase corresponding to the first trigger phrase. The computer program product further includes instructions for causing the computer to: prompt a user for at least one user-selected trigger phrase; prompt the user for user-selected standard text corresponding to the user-selected trigger phrase; and store the user-selected trigger phrase in association with the user-selected standard text for use in determining that the user-selected trigger phrase is present in the first transcription. The computer program product further includes instructions for causing the computer to: compare multiple edited medical transcriptions corresponding to multiple dictations; identify similar portions of the multiple medical transcriptions; determine an automatically-determined standard text block corresponding to the similar portions; and store at least one indication of texts from transcriptions of the multiple dictations corresponding to the similar portions as at least one automatically-determined trigger phrase corresponding to the automatically-determined standard text block. The computer program product further includes instructions for causing the computer to: determine presence of a second standard text block in an edited medical transcription; determine a second trigger phrase in a second medical transcription associated with the edited medical transcription, the second trigger phrase corresponding to the second standard text block; and store the second trigger phrase for use in determining presence of the second trigger phrase in another transcription. The instructions for causing the computer to determine that the first trigger phrase is present in the first transcription cause the computer to so determine if the actual phrase in the first transcription is within a threshold likeliness of being a possible form of the first trigger phrase. The computer program product further includes instructions for causing the computer to obtain the first trigger phrase based upon at least one of speaker and worktype associated with the dictation. The computer program product further includes instructions for causing the computer to display a list indicative of available standard text blocks including the first standard text block and providing descriptions of content of the available standard text blocks.

In general, in another aspect, the invention provides a language processor module for processing a medical dictation transcription, the module being configured to: compare words of the transcription with a trigger phrase associated with a standard text block; determine that the transcription includes the trigger phrase; and replace, if the transcription includes the trigger phrase, the content of the transcription corresponding to the trigger phrase with the standard text block in the transcription.

Implementations of the invention may include one or more of the following features. The module is further configured to insert text from the transcription proximate the text corresponding to the trigger phrase into the first standard text block. To insert text from the transcription, that is proximate the text corresponding to the trigger phrase, into the first standard text block, the module is configured to replace at least a portion of the standard text block with the text proximate to the text corresponding to the trigger phrase. To insert text from the transcription, that is proximate the text corresponding to the trigger phrase, into the first standard text block, the module is configured to fill a placeholder portion of the standard text block with the text proximate to the text corresponding to the trigger phrase. To determine that the transcription includes the trigger phrase, the module is configured to determine if the actual phrase in the transcription is within a threshold likeliness of being a possible form of the trigger phrase. The module is further configured to retrieve the trigger phrase from storage based upon at least one of speaker and worktype associated with the dictation.

In general, in another aspect, the invention provides a language processor module for processing a medical dictation transcription, the module being configured to: prompt a user for at least one user-selected trigger phrase; prompt the user for user-selected standard text corresponding to the user-selected trigger phrase; and store the user-selected trigger phrase in association with the user-selected standard text for retrieval and use in determining that the user-selected trigger phrase is present in a medical dictation transcription.

Implementations of the invention may include one or more of the following features. The module is further configured to: prompt the user for at least one of a speaker and a worktype to be associated with the user-selected standard text and the user-selected trigger phrase; and store the at least one of speaker and worktype in association with the user-selected standard text and the user-selected trigger phrase.

In general, in another aspect, the invention provides a language processor module for processing a medical dictation transcription, the module being configured to: compare multiple edited medical transcriptions corresponding to multiple dictations; identify similar portions of the multiple medical transcriptions; determine an automatically-determined standard text block corresponding to the similar portions; and store an indication of at least one portion of text from at least one of the transcriptions of the multiple dictations corresponding to the similar portions of the edited medical transcriptions as an automatically-determined trigger phrase corresponding to the automatically-determined standard text block for retrieval and use in determining that the automatically-determined trigger phrase is present in another medical dictation transcription.

Implementations of the invention may include one or more of the following features. To determine the automatically-determined standard text block, the module is configured to determine that the similar portions are above a threshold amount of being identical. The module is further configured to verify the similar portions by comparing at least one of the similar portions to at least one other transcription for a speaker of the multiple dictations to determine presence of another text portion similar to the at least one of the similar portions.

In general, in another aspect, the invention provides a language processor module for processing a medical dictation transcription, the module being configured to: determine presence of a standard text block in an edited medical transcription; determine a trigger phrase in a literal medical transcription portion associated with the edited medical transcription, the trigger phrase corresponding to the standard text block; and store the trigger phrase for use in determining presence of the trigger phrase in another transcription.

Implementations of the invention may include one or more of the following features. The module is configured to store a plurality of automatically-determined trigger phrases corresponding to the automatically determined standard text block. The module is further configured to store the automatically-determined trigger phrase in association with at least one of speaker and worktype.

In general, in another aspect, the invention provides a method of processing a medical record transcription, the method including obtaining a medical transcription of a dictation, the dictation being from medical personnel and concerning a patient, analyzing the medical transcription for presence of stored trigger phrases associated with standard text blocks, determining that a particular trigger phrase from the stored trigger phrases is present in the medical transcription if an actual phrase in the medical transcription has at least a threshold level of similarity to the particular trigger phrase, and replacing the content of the transcription corresponding to the trigger phrase with the standard text block if the transcription includes the trigger phrase.

Implementations of the invention may include one or more of the following features. The replacing results in an edited medical transcription, and the method further includes transmitting the edited transcription to the medical personnel before further editing, if any, by a medical transcriptionist if the edited medical transcription comprises at least a predetermined level of standard text from the standard text blocks. The method further includes providing a list of the standard text blocks to at least one of a medical transcriptionist and the medical personnel wherein the list provides descriptions of content of the standard text blocks.

Various aspects of the invention may provide one or more of the following capabilities. Time and cost of generating medical transcription documents can be reduced. Transcriptionist editing time can be reduced. Transcriptionist fatigue in editing transcribed documents can be reduced. Stress associated with typing/editing, including physical stress, can be reduced. Consistency in medical documentation can be improved. Efficiency of dictating can be improved. Requiring clinicians to explicitly dictate formatting instructions can be reduced or eliminated. The format of standard documents may be made uniform for a clinician or across a health care institution. Management of transcription workflow can be streamlined. Further, in a speech-recognition-assisted medical transcription system, the speech-recognition devices can have access to the latest version of standard text and documents for each clinician. Standard text can be pre-inserted into the draft transcription prior to review and editing by the MT.

These and other capabilities of the invention, along with the invention itself, will be more fully understood after a review of the following figures, detailed description, and claims.

BRIEF DESCRIPTION OF THE FIGURES

FIG. 3 is an exemplary user interface for prompting a registration of Standards for use in transcription.

FIG. 4A is an exemplary portion of a Standards table for use in determining triggers for transcriptions.

FIG. 4B is an exemplary portion of a speaker-Worktype Standards table for use in determining triggers for transcriptions.

FIG. 6 is an exemplary alignment table for use in identifying standards.

FIG. 10 is an exemplary initial interface for updating standard texts.

FIG. 11 is an exemplary secondary interface for updating standard texts.

DETAILED DESCRIPTION OF PREFERRED EMBODIMENTS

Embodiments of the invention provide techniques and a workflow for using automatic speech recognition of trigger phrases to insert standard text into medical transcription documents. Embodiments of the workflow include manual and automatic registering of speech triggers and output text, as well as techniques for improving the accuracy with which the appropriate triggers are detected. Embodiments of the invention may be applied to, e.g., background and front-end speech-recognition-assisted transcription systems. In embodiments of the invention, verbal trigger phrases are used as indicators that portions of pre-defined text are to be inserted into a transcription at a given location. In some embodiments, a trigger phrase specifies the entire content of the desired transcription. In other embodiments, a trigger phrase refers to a subset of the final document, and regular dictation is used to indicate the rest of the text. In other embodiments, a trigger phrase is used to indicate substantially all of either the entire document or a section of the final document, having "blanks" to fill in by subsequent dictation. Other embodiments are within the scope of the invention.

Figure 1:
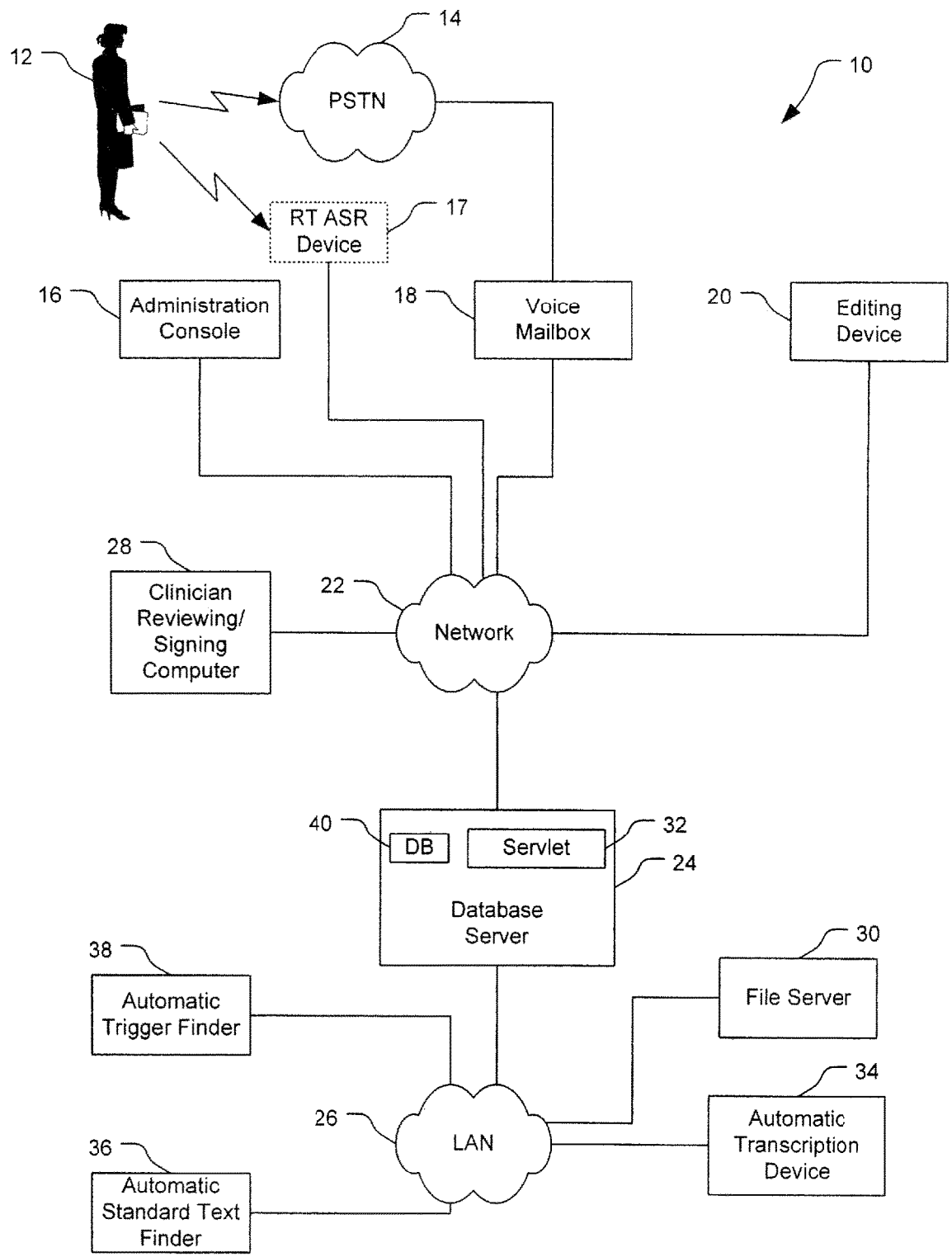
FIG. 1 is a simplified diagram of a system for transcribing dictations and editing corresponding transcriptions.

Referring to FIG. 1, a system 10 for transcribing audio and editing transcribed audio includes a speaker/person 12, a communications network 14, an administrative console 16, a real-time ASR device 17, a voice mailbox system 18, an editing device 20, a communications network 22, a database server 24, a communications network 26, a reviewing computer 28, a file server 30, an automatic transcription device 34, an automatic standard text finder 36 and an automatic trigger finder 38. Embodiments of the invention may have systems with more or fewer elements than the system 10, e.g., without the ASR device 17, as indicated by dotted lines. Here, the network 14 is preferably a public switched telephone network (PSTN) although other networks, including packet-switched networks could be used, e.g., if the speaker 12 uses an Internet phone for dictation. The network 22 is preferably a packet-switched network such as the global packet-switched network known as the Internet. The network 26 is preferably a packet-switched, local area network (LAN). Other types of networks may be used, however, for the networks 14, 22, 26, or any or all of the networks 14, 22, 26 may be eliminated, e.g., if items shown in FIG. 1 are combined or eliminated.

Preferably, the voice mailbox system 18, the administrative console 16, the real-time ASR device 17 and the editing device 20 are situated at the health care facility, remotely from the hosting facility where the database server 24 and the automatic transcription device 34 are located. These systems/devices 16, 17, 18, 20, 24, 34, however, could be located at the same site, with communications between them taking place, e.g., over a local area network. Similarly, it is possible to locate the automatic transcription device 34 at the health care facility, and have the device 34 communicate with the database server 24 over the network 22.

The network 14 is configured to convey dictation from the speaker 12 to the voice mailbox system 18. Preferably, the speaker 12 dictates into an audio transducer such as a telephone, and the transduced audio is transmitted over the telephone network 14 into the voice mailbox system 18, such as the Intelliscript™ product made by eScription™ of Needham, MA. The speaker 12 may, however, use means other than a standard telephone for creating the digital audio file for each dictation. For example, the speaker 12 may dictate into a handheld PDA device that includes its own digitization mechanism for storing the audio file. Or, the speaker 12 may use a standard "dictation station," such as those provided by many vendors, or via a microphone attached to a personal computer or other device. Still other devices may be used by the speaker 12 for dictating, and possibly digitizing the dictation, and sending it to the voice mailbox system 18.

The voice mailbox system 18 is configured to digitize audio from the speaker 12 to produce a digital audio file of the dictation. For example, the system 18 may use the Intelliscript™ product made by eScription.

The voice mailbox system 18 is further configured to prompt the speaker 12 to enter an identification code and a workType code. The speaker 12 can enter the codes, e.g., by pressing buttons on a telephone to send DTMF tones, or by speaking the codes into the telephone. The mailbox system 18 is further configured to store the identifying code and the workType code in association with the dictation. The identification code can associate the dictation with a particular speaker and/or an entity associated with the speaker (e.g., the speaker's employer or affiliate hospital, etc.). Speakers with multiple affiliations (e.g., to different entities such as hospitals) preferably have multiple identification codes, with each identification code corresponding to a respective one of the affiliated entities. The system 18 preferably prompts the speaker 12 to provide the workType code at least for each dictation related to the medical field. The workType code designates a category of work to which the dictation pertains, e.g., for medical applications this could include Office Note, Consultation, Operative Note, Discharge Summary, Radiology report, etc. The workType code may be used to define settings such as database fields and/or to refine settings, such that settings may be specific to the workType of dictations provided by the speaker, and/or to other parameters or indicia.

The voice mailbox system 18 is further configured to transmit the digital audio file and speaker identification code and workType code over the network 22 to the database server 24 for storage. This transmission is accomplished by the system 18 product using standard network transmission protocols communicating with the database server 24.

The database server 24 is configured to store the incoming data from the voice mailbox system 18, as well as from other sources, in a database 40. The database server 24 may include the EditScript™ database product from eScription. Software of the database server is configured to produce a database record for the dictation, including a file pointer to the digital audio data, and a field containing the identification code for the speaker 12. If the audio and identifying data are stored on a PDA, the PDA may be connected to a computer running the HandiScript™ software product made by eScription that will perform the data transfer and communication with the database server 24 to enable a database record to be produced for the dictation.

Preferably, all communication with the database server 24 is intermediated by a "servlet" application 32 that includes an in-memory cached representation of recent database entries. The servlet 32 is configured to service requests from the voice mailbox system 18, the automatic transcription device 34, the editing device 20, and the administrative console 16, reading from the database 40 when the servlet's cache does not contain the required information. The servlet 32 includes a separate software module that helps ensure that the servlet's cache is synchronized with the contents of the database 40. This enables the database 40 to be off-loaded of much of the real-time data-communication and to grow to be much larger than otherwise possible. For simplicity, however, the below discussion does not refer to the servlet, but all database access activities may be realized using the servlet application 32 as an intermediary.

The automatic transcription device 34 may access the database 40 in the database server 24 over the data network 26 for transcribing the stored dictation. The automatic transcription device 34 uses an automatic speech recognition (ASR) device (e.g., software) to produce a draft transcription for the dictation. An example of ASR technology is the AutoScript™ product made by eScription, that also uses the speaker and worktype identifying information to access speaker-worktype-dependent ASR models with which to perform the transcription. The device 34 can transmit the draft transcription and/or intermediate results over the data network 26 to the database server 24 for storage in the database 40 and to be accessed, along with the digital audio file, by the editing device 20.

The automatic trigger finder 38 is configured to access the database 40 in the database server 24 and to use data stored in the database to determine standards triggers used by particular speakers. For example, the automatic trigger finder 38 may access literal transcriptions and corresponding edited transcriptions, as well as registered standard texts, for a speaker or speaker-workType combination. The automatic trigger finder 38 is configured to determine verbal triggers that are used by speakers to indicate that standard text is to be inserted, e.g., by identifying similar words and/or phrases in dictations that correspond to standard text in final, edited document versions. Triggers are stored in association with the speaker, workType or speaker-workType combination in the database 40.

The automatic standard text finder 36 is configured to access the database 40 in the database server 24 and to use data stored in the database to determine unregistered standard text used by particular speakers. For example, the automatic standard text finder 36 may access edited transcriptions for a speaker or speaker-workType combination. The automatic standard text finder 36 identifies occurrences of identical or nearly identical text in multiple edited transcriptions that have not been registered by a user and alerts the user that the occurrences of such text exist, in association with the speaker, workType or speaker-workType combination in the database 40. The text finder 36 can request registration of the repeated text and identify possible trigger words/phrases and request other triggers.

The editing device 20 is configured to be used by a transcriptionist to access and edit the draft transcription stored in the database of the database server 24. The editing device 20 is configured to access standards in the database 40 that are specific to the speaker-worktype of the document being edited and to insert the standard text into the document, e.g., in place of a trigger word/phrase. The editing device 20 includes a computer (e.g., display, keyboard, mouse, monitor, memory, and a processor, etc.), an attached foot-pedal, and appropriate software such as the EditScript Client™ software product made by eScription. The transcriptionist can request a dictation job by, e.g., clicking an on-screen icon. The request is serviced by the database server 24, which finds the dictation for the transcriptionist, and transmits the corresponding audio file and the draft transcription text file, as stored in the database.

The transcriptionist edits the draft using the editing device 20 and sends the edited transcript back to the database server 24. For example, to end the editing session the transcriptionist can click an on-screen icon button to instruct the editing device 20 to send the final edited document to the database server 24 via the network 22.

With the data sent from the editing device 20, the database in the server 24 contains, at least for each dictation: a speaker identifier, a workType identifier, the digital audio signal, the literal text document, the draft document and the edited text document.

The edited text document can be transmitted directly to a customer's medical record system or accessed over the data network 22 from the database by the administrative console 16. The console 16 may include an administrative console software product such as Emon™ made by eScription.

Figure 2:
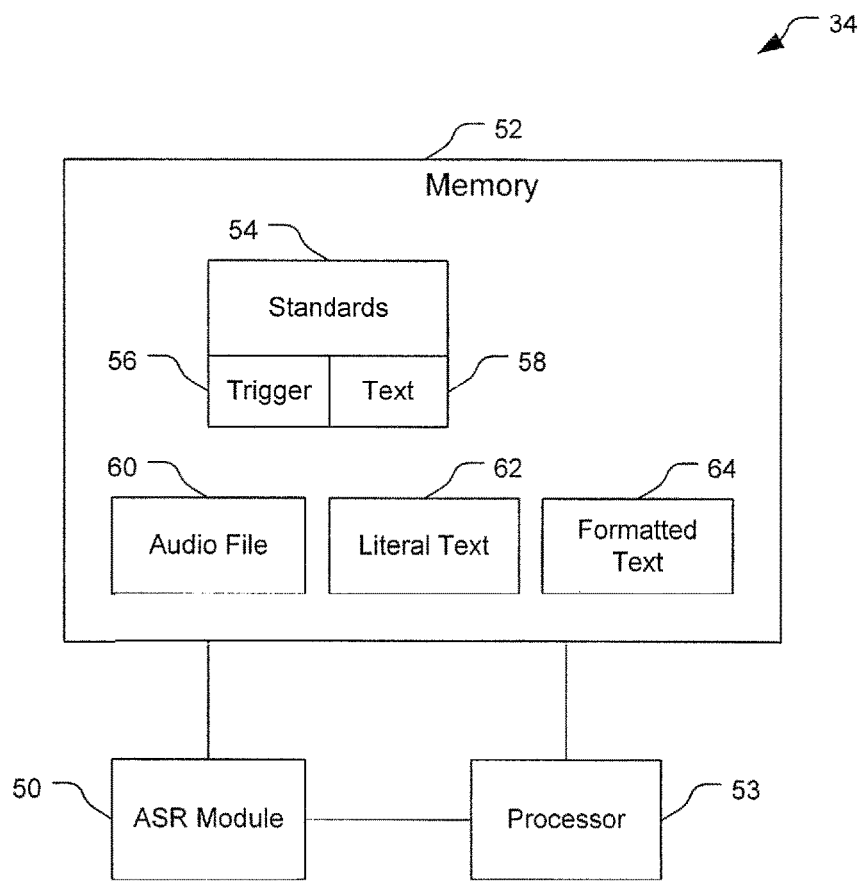
FIG. 2 is a simplified diagram of an automatic transcription device for use in creating draft transcriptions for editing.

Referring also to FIG. 2, the automatic transcription device 34 includes an ASR module 50, memory 52 and a processor 53 for reading software code stored in the memory 52 and/or in the ASR module 50 and for executing instructions associated with this code for performing functions described below. The ASR module 50 downloads a digital audio file 60 from the database 40. The ASR module 50 also obtains information related to the dictation, such as the speaker, workType, etc. The ASR module 50 downloads acoustic and language models from the database 40. Preferably, the acoustic and language models are specific to the speaker or speaker-worktype of the dictation. The ASR module 50 is configured to create a literal transcription 62, or literal text file, from the audio file 60. The ASR module 50 is further configured to obtain standards 54 from the database 40 and store the standards 54 in the memory 52. A standard 54 comprises a trigger phrase or phrases 56 and standard text 58. The standards 54 (see FIGS. 4A and 4B and associated text) are stored in the database 40 to be accessed in conjunction with a particular dictation, e.g., in association with a speaker, a workType or a combination of speaker and workType. A speaker or a speaker-workType may have one or many standards 54, which is downloadable by the ASR module 50.

The ASR module 50 is configured to search the literal transcription 62 for words and/or phrases corresponding to (e.g., matching) a standard trigger 56, for example, using a pattern-comparison technique. The ASR module 50 replaces a spoken word/phrase with the corresponding standard text 58 when the spoken words/phrases correspond to (e.g., match, or match within a threshold of confidence) a trigger 56. The formatted text, or output draft transcription 64 is comprised in general of literal text, optionally processed by the formatting models and software, and inserted standard text 58. The output draft transcription may be comprised entirely of one or more inserted standard texts 58, with all of the literal text replaced. Or, if no triggers are found, the output draft transcription will contain the literal text, optionally processed by the formatting models and software.

Figure 5:
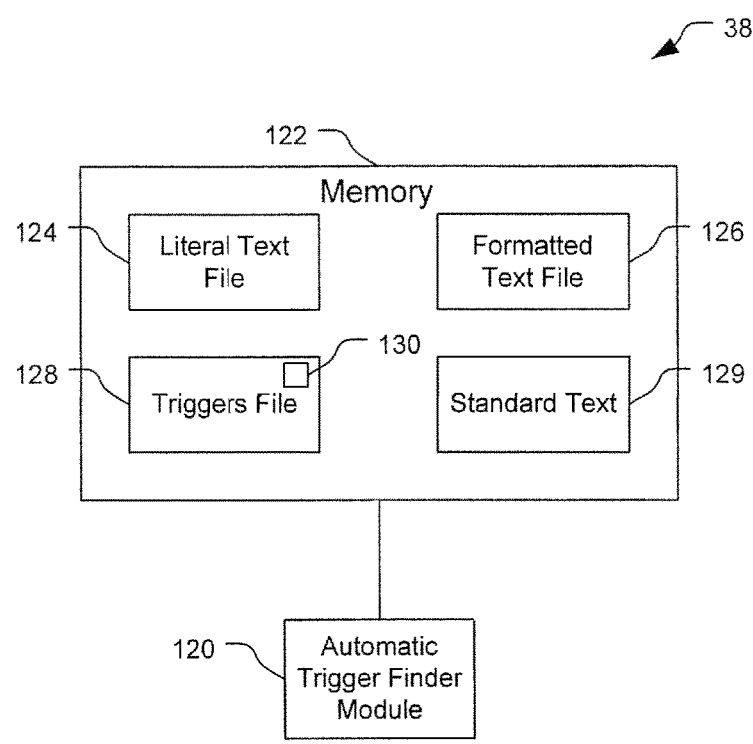
FIG. 5 is a simplified diagram of an automatic trigger finder device for use in developing standards for transcriptions.

The ASR module 50 uploads the literal text 62 and output draft transcription 64 to the database 40. The output draft is accessed by an MT who edits the draft and produces the final document. The literal text 62 is used for the alignments used in the process which automatically creates and adapts standards triggers 101 (see FIGS. 5 and 6, and accompanying text).

Referring also to FIG. 3, the administrative console 16 is configured to register standards 54 that are used by the ASR module 50 to insert standard text into transcriptions. Standards 54 are registered via the administrative console 16. For example, standards 54 may be manually entered into the system 10. A user interface 80 includes a speaker field 82, a workType field 84, a text field 86, a description field 87, and trigger fields 88. The user interface 80 further includes a filename browser 90 and a submit button 92. The user interface 80 prompts a user (e.g., a clinician, transcription manager, health information systems director, etc.) to input at least one speaker name or workType, a description text, at least one trigger-phrase and the name of a file that contains the standard text to be associated with the trigger phrase(s). The file can be, for example, on a file server that is connected to the database 40, or a file on a user's computer that is uploaded to the database 40 for storage either in the database or on a file server connected to the database 40.

After entry of the requested information, the user clicks the "submit" button 92. The information is uploaded to the database 40, and the relevant database records are populated with fields representing the association between the trigger phrase(s) 88, the description 87 and the standard text file 90. If text has been entered into the text field 86, then in response to actuation of the submit button 92, a new file is generated on the file server 30 that contains the text in the field 86. Referring to FIG. 4A, a database table 100 stores the description/trigger/standard text file triples 102, each with an index 104. Each triple 102 submitted through the registration process has an entry in the database table 100 (i.e., if either the trigger phrase, description or standard text differs, a new record, with a new index, is added to the table 100).

Referring to FIG. 4B, a speaker-workType-standards table 110 stores a speaker ID 112, a workType 114 and standards 116. The standards 116 are listed according to the index 104. Every speaker-workType using the system 10 has an associated list of standards field 116. The system 10 can use information about a speaker and workType for a dictation under analysis and the table 110 to limit the trigger phrases searched for in the dictation for possible replacement with standard text.

The administrative console 16 is configured to check the database table 100 to determine if the submitted standard identified by its index 104 already exists (e.g., a standard having the same trigger-phrase and output text). If so, the standards index 104 is used to represent that entry in the standards table 110. If not, the administrative console 16 is configured to add a new record to the database table 100 with the trigger-phrase 88, description 87, and standard text file 90 (or the text file created as a result of text entry 86) triple 102, and an index 104 is generated and used to represent that entry in the database table 100. For each speaker-workType in the speaker-workType-standards table 110 that matches, the standards index 104 is added to the list-of-standards field 116. For example, multiple speakers, or even all speakers with a given workType may share a particular standard text and associated description, or use identical trigger phrases to indicate that they should be inserted by the ASR module 50 (see FIG. 9 and related text). The standard text files 90 in the database table 100 may be used by MTs at the editing device 20 when they are typing transcriptions from the audio, with or without speech recognition drafts. This may be accomplished at the editing device 20 by, for example, clicking on a button or typing a hot-key sequence which indicates that a menu of standards for the appropriate speaker-worktype should appear, with each menu item displayed as the description for the associated standard text file. When the MT clicks on a given description, the contents of the standard text file are inserted in the transcription document at the current cursor location.

Trigger phrases 101 in the database table 100 may be encoded as regular expression grammars. For example, a trigger-phrase may be written as:

[Please] (use|insert|include) [(my|the)] (normal|standard) chest [(template|document|macro|text)] [here].

where parentheses indicate choices and square brackets indicate options. For example, any of the following language matches the trigger phrase 101 in the databse table 100:

"Please use my normal chest."
"Insert the standard chest template."
"Please include normal chest macro."
"Use my standard chest here."

Variants may be generated automatically using known natural-language processing techniques, and inserted into the database 40.

During the standards registration process using the user interface 80, portions of the standard text which may be filled in as a result of a trigger phrase can be marked using, for example, XML tags such as:

<fieldN> . . . </fieldN>, where N is a field number and text may be represented as either normal text or a "blank", represented, for example, by three successive underscore characters. For example, a "normal physical examination" standard text may look like this:

PHYSICAL EXAMINATION:
GENERAL APPEARANCE: <field1>_____</field1>
HEIGHT: <field2>_____</field2>
SKIN: <field3> Normal color, texture, no rash. </field3>
WEIGHT: <field4>_____</field4>
HEAD: <field5> Normal shape, fontanel open. </field5>
. . .

The specification of the trigger phrase for this standard text uses a separate sub-trigger for each field specified in the text. After specifying the overall trigger, e.g., "Insert my normal physical exam template," and clicking the "submit" button 92, the standard text is analyzed for occurrences of the <field> tags, and the user is presented with a new data entry screen to provide triggers for each of the fields:

field1: "For general appearance, put"
field2: "Height is"
field3: "For skin, put"
field4: "Weight is"
field5: "For head, put"
etc.

Thus, the literal transcription:

"Please use my normal physical exam except for general appearance put healthy, well-nourished, well-appearing adult female in no acute distress and for head use normocephalic, atraumatic, with a height of five feet seven inches and weight is one hundred thirty nine pounds."

results in the following output draft transcription:

PHYSICAL EXAMINATION:
GENERAL APPEARANCE: Healthy, well-nourished, well-appearing adult female in no acute distress.
HEIGHT: 5 feet 7 inches
SKIN: Normal color, texture, no rash.
WEIGHT: 139 pounds.
HEAD: Normocephalic, atraumatic.

Referring to FIGS. 1 and 10-11, the administrative console 16 is further configured to modify or update existing standard texts. Initially, the administrative console 16 presents a user with a speaker/worktype selection screen 180. The screen 180 prompts the user to enter the speaker in a speaker window 182 and/or the worktype in a worktype window 184. In response to entry of information by the user into the appropriate window(s) 182, 184, and actuation of a submit button/icon 186, the administrative console 16 displays a standard selection/update screen 190 for the user. The screen 190 presents the user with a list 191 of standard text files 192 and their associated descriptions 193 corresponding to the speaker and/or worktype entered using the screen 180. The user can select one of the standard text files as indicated by an "X" 194, and the administrative console 16 will display the corresponding standard text in an editing/updating region 195. The console 16 is configured to prompt the user to edit/update the text in the region 195 as desired, e.g., by adding and/or removing text displayed in the region 195 and/or by changing the text file 192 corresponding to a description 193. The trigger(s) preferably remain the same for a given description 193. The revised text can be accepted by actuation of a submit button/icon 196, causing the standard text in the table 100 (FIG. 4A) to be replaced with the new text in the region 195.

Referring to FIGS. 1, 4A-4B and 5, in addition to standards registration and updating, the literal and edited versions of a transcription may be used by the automatic trigger finder 38 to produce standard triggers for the speaker or workType for a given standard text. The literal and edited versions of transcriptions associated with their respective standard text, speaker and workType identifiers are stored in the database 40. The automatic trigger finder 38 accesses the database 40 in the database server 24 to use data stored in the database 40 to determine verbal triggers used by particular speakers to indicate that the given standard text is to be inserted. The automatic trigger finder 38 uses the literal and the edited transcriptions for each speaker or workType, or combination of both speaker and workType to build standards triggers for the speaker (and/or speaker and workType). These triggers are stored in the database 40 for access and use by the automatic transcription device 34 to indicate that standard text is to be inserted in a document.

The automatic trigger finder 38 is configured to develop the triggers 101 that are stored in the database 40 for access by the ASR module 50. The automatic trigger finder 38 includes an automatic trigger finder module 120 and a memory 122. The automatic trigger finder module 120 includes memory storing software code and a processor for reading this software code and executing instructions associated with this code to perform functions described below. The memory of the module 120 and the memory 122 may be portions of a single physical memory. The memory 120 includes a literal text file 124, an edited text file 126, a triggers file 128, and a reference standard text 129. The literal text file 124 includes literal transcriptions that are produced from the dictated audio by the ASR module 50. The edited transcriptions file 126 includes formatted text associated with a draft transcription that has been edited by a transcriptionist and stored in the database 40. The triggers file 128 includes triggers 130 extracted from a comparison of the literal text to the edited text, with reference to the standard text 129, which is passed in as a parameter of the process. As with the manual trigger entry process (FIG. 3), automatically found triggers 130 are used by the ASR device 50 to map verbal directives from the speaker 12 into standard text segments.

The automatic trigger finder module 120 is configured to discover standards triggers 130 based on the literal text in the literal text file 124 in comparison with the formatted text, including standard text, from the transcriptionist-formatted text file 126 for corresponding transcriptionist-edited documents.

The automatic trigger finder module 120 is configured to align the literal text file 124 with the formatted text file 126 for a set of dictations (hereinafter referred to as a parallel text set) and to segment this alignment using the standard text 129 to develop the triggers 130. A parallel text set could include multiple literal and formatted text files 124, 126 corresponding to multiple dictations. The module 120 is configured to align the literal text and the transcriptionist-edited text of the parallel text set to determine what portions of the literal text can be automatically replaced by standard text with minimal interaction from a transcriptionist. Alignment is accomplished using, for example, a standard technique such as reducing (possibly minimizing) the Levenshtein distance between the literal text and the edited text, using a modified Levenshtein distance that weights certain substitution errors more or less than normal based on task specific knowledge, etc. The module 120 is configured to determine the literal triggers for each portion of the alignment where the edited text matches the standard text 129. In general, a parallel text set comprising multiple dictations will produce multiple segmentations which correspond to the standard text 129 and will therefore produce multiple triggers 130 to store in the triggers file 128.

Referring also to FIG. 6, an exemplary alignment table 140 illustrates the alignment of literal text 124 to edited text 126 along with the segmentation by reference to the standard text 129 for producing a trigger 130. The alignment table 140 includes automatic speech recognition columns 142, 143 and formatted entries columns 144, 145. A literal text statement is represented as the ASR entries 142 and is transcribed from the audio dictation. The formatted text entries 144 represent the formatted document that results from editing the literal text in the ASR field 142. Here, the region between lines 30 and 66 has been demarcated as it corresponds to a given standard text. The alignment of the columns 142, 143 with the columns 144, 145, shows that the clinician used the phrase "use my normal exam template here" to indicate that standard text (as shown in the columns 144, 145) was to be inserted.

The automatic trigger finder 120 may find triggers 130 which are not exactly the spoken language, but are representative of typical errors made by the ASR device 50 when producing the literal transcription of the audio. For example, the ASR column 142 may contain the sequence "use the normal exam macrophage" instead of "use my normal exam macro here", but the misrecognized phrase is added as a trigger phrase 130.

Figure 12:
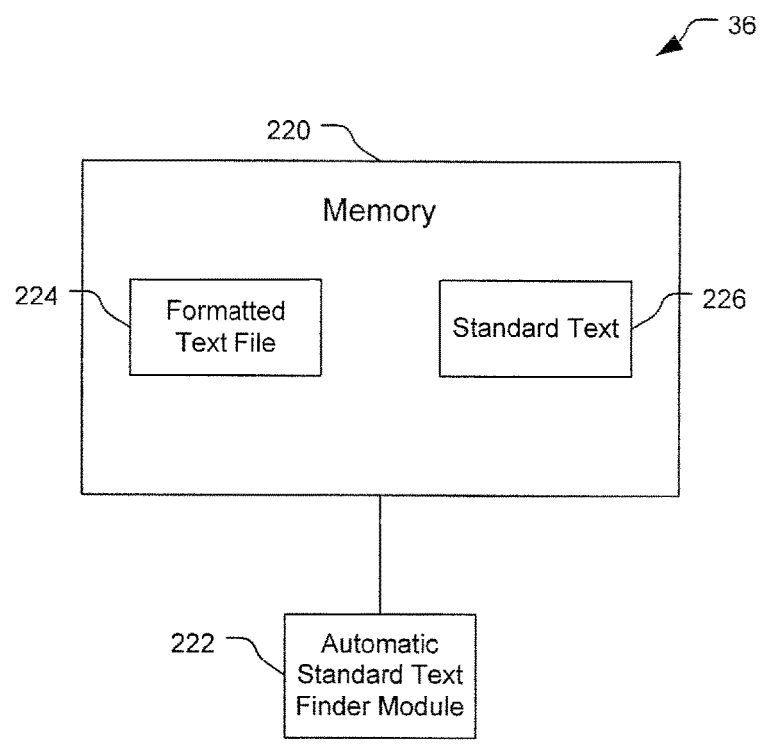
FIG. 12 is a simplified diagram of an automatic standard text finder shown in FIG. 1.

Referring to FIGS. 1 and 12, the automatic standard text finder 36 includes a memory 220 and an automatic standard text finder module 222. The automatic standard text finder module 222 includes memory storing computer-readable software code and a processor for reading this software code and executing instructions associated with this code to perform functions described below. The processor can be dedicated to the text finder 36, or may be shared with other apparatus such as the trigger finder 38. The memory of the module 222 and the memory 220 may be portions of a single physical memory. The memory 220 includes a formatted text file 224, that contains formatted texts, and a standard text file 226, that contains standard texts. The standard text finder module 222 is configured to align formatted texts in the file 224 with each other. The module 222 is configured to identify and demarcate (similar to identification and demarcation shown in FIG. 6) regions of similar (e.g., identical, near-identical, etc.) aligned text. The module 222 will add one of the similar regions of text to the standard text file 226. The module 222 is configured to compare the standard texts in the text file 226 with the formatted texts in the formatted text file 224 to determine the number of occurrences (absolute or relative, e.g., frequency of occurrences per number of texts reviewed) of each standard text in the file 226 in the reviewed formatted texts. The module verifies/approves of standard texts exceeding a corresponding threshold (e.g., for quantity and/or frequency). The module 222 is further configured to upload verified/approved standard texts from the file 226 to the database table 100 (FIG. 4A), with an index. One or more triggers can be provided for and associated with the standard texts automatically or manually as discussed herein.

Figure 7:
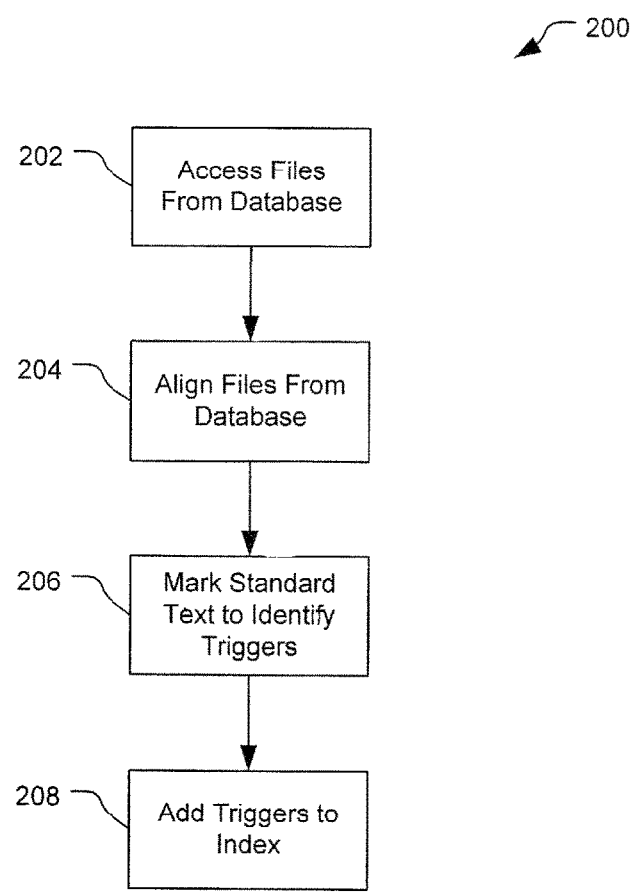
FIG. 7 is a block flow diagram of a process of developing a trigger using the automatic trigger finder.

Referring to FIG. 7, with further reference to FIGS. 1-6, a process 200 for developing a trigger 130 using the automatic trigger finder 38 includes the stages shown. The process 200, however, is exemplary only and not limiting. The process 200 can be altered, e.g., by having stages added, removed, or rearranged. The process 200 is preferably performed for each occurrence of known standard text in the standards table 110 for a given speaker (or speaker-worktype) appearing in the final formatted transcription, and is preferably performed for each occurrence of a speaker-worktype in the table 110.

At stage 202, the automatic trigger finder module 120 queries the database 40 for text that has been received into the system 10. For example, the automatic trigger finder module 120 may query for a set of all literal and final transcriptions related to a particular speaker, workType, or speaker/workType pair, for which a particular standard text occurs in the final transcription.

At stage 204, for each set of literal and final transcriptions, an alignment is made. The literal and final texts are put into columns (e.g., the columns 142, 143, 144, 145 of the table 140) with one word (or a null) per row. Similar words in the two columns are put in common rows with nulls inserted in the columns as appropriate to align the similar words.

At stage 206, the location of standard text is demarcated to identify the trigger. At stage 206, the trigger 130 is identified as the sequence of non-NULL tokens in the draft columns 142, 143 of the alignment that aligns with the section marked as standard text in the formatted columns 144, 145.

In embodiments of the invention, the process 200 may discover cases where standard text is being dictated fully, without the use of a trigger 130. For example, the alignment in these instances would largely comprise identical entries in the draft and edited columns 142, 143, 144, 145 of FIG. 6. From this, clinicians may be alerted that they can save time by using an existing or newly-registered trigger phrase 130 to indicate the insertion of the standard text, and can register manual trigger phrases 88 using the administrative console interface 80 shown in FIG. 3 to correspond with the standard text.

In embodiments of the invention, the process 200 may discover cases where standard text is being triggered, but has not been registered using the interface 80 shown in FIG. 3. For example, the process 200 may be invoked for registered standard texts that occur in the database table 100, independent of their speaker-worktype association. In this case, the database 40 is queried for documents for a speaker or speaker-worktype that contain the given standard text. The automatic trigger finder 38 searches for triggers 130 and, if any triggers 130 are discovered, they are added to the database table 100, with a new index into the table 100, and are associated with the given standard text file. An entry is added to the standard list 116 in the row of the table 110 corresponding to the speaker-worktype, or a new row is added to the table 110 if the speaker-worktype does not currently exist in the table 110.

At stage 208, triggers 130 are collected and added to the regular-expression trigger in the table 100. New entries may be added to the database table 100 where the standard text is the same as an existing entry, but with the new trigger 130, and the index 104 for this entry in the standards table 110 may be added to the speaker-workType-standards table entry in the standards table 110. Alternatively, existing triggers 101 may be extended to include the new triggers 130 using well-known regular-expression grammar notation, such as Backus Naur form.

Figure 8:
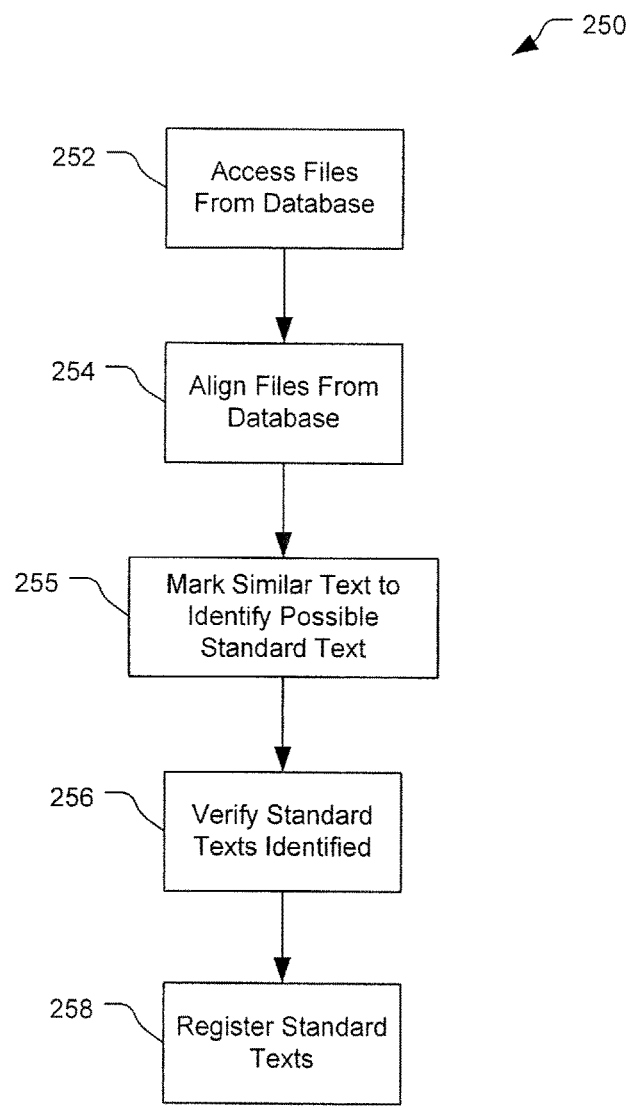
FIG. 8 is a block flow diagram of a process of identifying standard text using an automatic standard text finder.

Referring to FIG. 8, with further reference to FIGS. 1-6 and 12, a process 250 for discovering standard text automatically using the automatic standard text finder 36 includes the stages shown. The process 250, however, is exemplary only and not limiting. The process 250 can be altered, e.g., by having stages added, removed, or rearranged. Further, the process 250 may be performed before and/or after the process 200 for developing a trigger, e.g., such that the process 200 can develop triggers for standards discovered during the process 250.

At stage 252, for each speaker (or speaker-worktype), a sample of final edited transcriptions is collected from the database 40. For example, 100 transcriptions for a particular speaker can be collected from the database 40.

At stage 254, the sample transcriptions are aligned with each other. During alignment, text blocks that match exactly or nearly exactly (within a desired tolerance), are collected as standard text that a clinician may register as a standard having a trigger. For example, text blocks of about 50 words may be analyzed, although other block sizes may be used, but are at least large enough such that the use of a trigger phrase represents a time-savings for the clinician. Also, as a match between two transcriptions may not be identical, a threshold for how much identical matching of the text between transcriptions will cause designation as standard text is used. For example, matches of language of greater than about 90% of all of the words in text blocks can result in a text block being labeled as standard text. In an alternative embodiment, a clinician's final edited text documents—or a sample thereof—may be compared with the registered standard texts from other clinicians in the Standard table.

At stage 255, similar portions of aligned texts are demarcated and designated as possible standard texts. Text portions that are more than a threshold amount (e.g., about 90%) of being identical are marked as possible standard texts. The portions identified at stage 254 as being possible standard texts are marked or otherwise identified by the standard text finder module 222 in the aligned texts. The standard text finder module 222 selects one of the identified text portions and stores this selected text portion in the standard text file 226 for verification as standard text.

At stage 256, a verification is performed. A search is performed in (preferably all of) the clinician's final documents, not just the subset sample selected at stage 254, for standard texts. The text finder module 222 compares the possible standard texts in the text file 226 with the formatted texts to find text portions similar (e.g., about 90% or more identical) to the possible standard texts in the text file 226. The automatic standard text finder 36 can verify standard texts, and preferably does so only for standard texts that occur in a given fraction of all the documents and that would be the best candidates for registration.

At stage 258, the standard texts are registered. The standard texts are presented to the clinicians that are using these texts either by dictating them fully, or by triggering them. When registered, the standard texts become entries in the standards table 100 and triggers are created for these entries.

Figure 9:
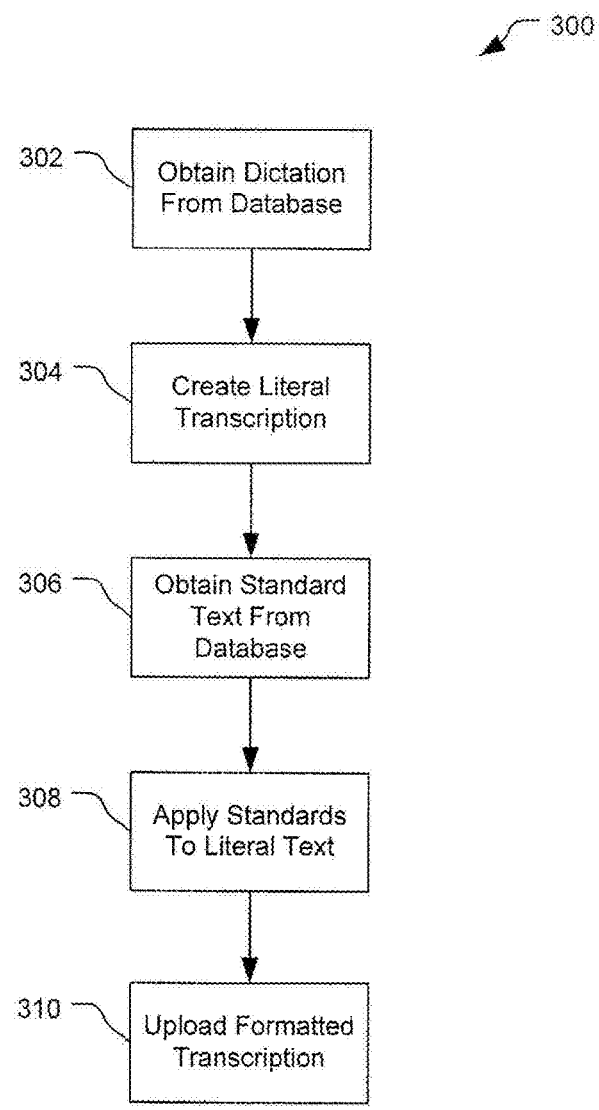
FIG. 9 is a block flow diagram of a process of automatically transcribing a dictation using triggers to insert standard text.

Referring to FIG. 9, with further reference to FIGS. 1-6, a process 300 for inserting standard text into a transcribed document includes the stages shown. The process 300, however, is exemplary only and not limiting. The process 300 can be altered, e.g., by having stages added, removed, or rearranged.

At stage 302, a dictation is obtained from the database 40. The speaker 12 dictates text that is conveyed through the network 14 to, and stored in, the voice mailbox 18. The dictation is conveyed through the network 22, the database server 24, and the LAN 26 to the automatic transcription device 34. The dictation is associated with a speaker and/or workType an indication of which is stored, in association with the dictation, in the database 40.

At stage 304, a literal transcription is created from the dictation. The ASR device 34 transcribes the speech of the speaker 12 to produce a literal transcription and stores this transcription locally for analysis regarding standard text portions.

At stage 306, a trigger 56 is obtained by the ASR device 34 for use in searching for standard texts. The trigger 56 is found using information regarding the speaker, workType, or speaker/workType combination parameter that is associated with the selected dictation.

At stage 308, the literal transcription is searched for matches to the trigger 56 to replace the trigger literal text with the standard text 58. To apply the standard text 58, the literal text file 62 is searched for a literal portion of text that corresponds to a registered standard trigger 56. If a match (within acceptable tolerance/confidence) is made, the standard text 58 is applied such that the literal text portion 62 is replaced with the standard text 58. Triggers 56 are registered, for example, according to processes described in FIGS. 7 and 8. Triggers are also registered by manual entry of triggers and corresponding standard text, for example by a clinician or a manager. An auto-formatted text document 64 is developed from the application of the standards 58 to the literal text file 62. At stage 310, the formatted transcription and the literal text transcription are uploaded to the database 40 for storage.

Other embodiments are within the scope and spirit of the appended claims. For example, due to the nature of software, functions described above can be implemented using software, hardware, firmware, hardwiring, or combinations of any of these. Features implementing functions may also be physically located at various positions, including being distributed such that portions of functions are implemented at different physical locations. For example, the translation model builder 29 may be disposed wholly or partially elsewhere, such as at the database server 24.

How and whether trigger literal text is replaced with the appropriate standard text may depend on the type of standard, as determined during the registration process. The literal transcription is searched for "except" triggers (e.g., "except," "but," "however," etc.). If an except trigger is found, then the standard text 58 replaces the trigger literal text except that the portion of the standard text 58 to which the except trigger is applicable is replaced with the literal text associated with the except trigger. Each replacement field in standard text has associated with it a set of potential except triggers. If an acceptable match is found to the except trigger, then the value for the replacement field is filled in to the draft transcription, the blank or pre-existing standard text is removed, and the literal text following the except trigger (potentially formatted, e.g. as numeric quantities) is inserted, and the trigger literal text is removed. Further, if the standard text includes blanks (e.g., empty fields or placeholders for certain information, e.g., temperature, pulse, blood pressure, etc.), then the literal text near the trigger phrase may be used to fill in the missing information. For example, a normal exam standard text may have placeholders for the patient's temperature, pulse, and blood pressure. The literal text, "Use my normal checkup with 140 for weight, 98 point 4 degrees for temperature, pulse 65, and BP 120 over 90" may result in the following output draft transcription:
PHYSICAL Examination:
GENERAL APPEARANCE: No signs of acute illness.
WEIGHT: 140 pounds.
TEMPERATURE: 98.4.
RESTING PULSE: 65.
BLOOD PRESSURE: 120/90.

The output draft transcription may be encoded as a token-alignment file that may contain invisible records for annotation purposes. This file would comprise a set of token records, with each record preferably containing a token, a begin index, and an end index. The token comprises a character or a sequence of characters that are to appear on the screen during a word-processing session, or one or more sounds that may or may not appear as text on a screen. A begin index comprises an indication of the beginning of a standard text block and the end index comprises an indication of the end of the standard text block. As an alternative, the end index may not exist separately if second standard text block follows a first standard text block, with it being assumed that the starting point of the second text block is also the ending point of the previous text block. The transcription device 30 can store the token-alignment file in the database 40. The token-alignment file may be encoded with the locations at which standard-text was inserted using invisible "markup" such as <std3> . . . </std3>, where the particular Standard is indicated by the index in these tags. This may be used as part of the standards updating process, for example as an aid to definitively demarcate the portion of the alignment associated with a standard and therefore to better produce the automatic triggers 130.

The ASR device may be configured so that when certain standards are inserted, the transcription goes directly to the clinician for signing. For example, this may be done if substantially all of the output transcription resulted from the insertion of standard text. The output transcription may still be sent to the database 40, but its state marked as "Ready for Signing," instead of the usual "Ready for Editing." At a later time, the draft may be accessed by a dictating clinician at the clinician's own computer terminal for review and signing, prior to being uploaded as the final, signed document into the database 40. The computer at which the signing takes place may also have editing capabilities, so that the clinician may update the document prior to signing. Several means are available for this editing process, e.g., standar PC-based editors, textual tokens, or real-time speech recognition, and these means may be employed in various combinations. Standard PC-based editors may be used to modify the text by keyboard and mouse. Certain textual tokens in the draft transcription may have associated with them several options from which the speaker-now-editor may easily select, by, for example, clicking a mouse over the item which causes a menu of the options to be presented, and then choosing the particular option by clicking the mouse again. This means may be particularly useful for editing drafts in which "standards except" have been inserted, in the event that the ASR device was unable to determine which option was indicated verbally. This may happen, for example, either because the speaker did not indicate the choice at the original dictation time or because the literal transcription was erroneous so that no match was made against the clinician's standard trigger phrases. In this case, the choices may be included in the hidden records of the draft transcription using, for example, HTML or other well-known markup languages. Real-time speech recognition means may be provided at the signing computer and well-known interactive voice-editing means may then be employed to edit the document, as desired.

In some embodiments of the invention, the ASR process is accomplished at a real-time ASR device. The ASR software may reside on a computer that is directly connected to the dictating device, and the ASR process may run in parallel to the dictation. Thus, the literal words appear on the screen as they are dictated. As the literal words are decoded on the screen, the pattern matching search for standards is ongoing. When a standard is triggered, the literal trigger is erased and replaced by the appropriate standard text. This may facilitate signing of the transcription soon, if not immediately, after the draft transcription is produced, with no intermediate database transaction performed.

In still other embodiments, the ASR device resides on a local-area-network with the speaker's dictating device, and the audio data is quickly transmitted to the ASR device. Downloading of standards begins as the clinician begins dictating, as identifying information (speaker and/or work-Type) is sent to the ASR device prior to the audio stream. Replacement of standard text occurs on the ASR device in parallel to the incoming audio stream. When the clinician signals that the clinician is done dictating (for example, by pressing a button on a dictation device), the ASR device completes its processing, and the output draft transcription is sent to the computer terminal at the dictation station.

In embodiments involving real-time or near-real-time ASR, where the speaker is potentially involved in the editing of the final document, a user-interface may be provided to enable the speaker to manually insert standard text into the document. This may be used, for example if the literal transcription 62 fails to match one of the standards triggers 56. In this case, the speaker may press a button on the dictating device (e.g. a microphone) itself, and this will cause the menu of standard descriptions associated with the speaker or speaker-worktype to appear on the computer screen, at which point the speaker may select the appropriate standard description from the menu either by keyboard or voice interaction with the menu.

While the description above focused on medical transcriptions, the invention is not limited to medical transcriptions. The invention may be applied to formatting dictations for non-medical applications such as legal dictations, psychological evaluations, etc. Further, while the discussion above refers to "the invention," more than one invention may be disclosed.

What is claimed is:

1. A method comprising:
 analyzing, by a device, a set of medical transcriptions to identify a text block, wherein analyzing the set of medical transcriptions comprises determining that the text block occurs in a plurality of medical transcriptions within the set of medical transcriptions;
 storing in at least one structured datastore, by a device, a datastore record identifying the text block and an associated trigger, the trigger being an indicator causing automatic insertion of the text block within another medical transcription when the trigger is present in the other medical transcription, the at least one datastore storing a plurality of datastore records identifying a plurality of pairs of text blocks and associated triggers;
 detecting, from the other medical transcription, information corresponding to the trigger;
 automatically inserting the text block in a position within the other medical transcription based on the detection; and
 verifying modification of the other medical transcription via the insertion of the text block, wherein verification comprises determining an accuracy of the insertion of the text block.

2. The method of claim 1, wherein analyzing the set of medical transcriptions to identify the text block comprises analyzing the plurality of medical transcriptions for text that satisfies one or more criteria for similar text.

3. The method of claim 1, wherein analyzing the set of medical transcriptions to identify the text block comprises analyzing the plurality of medical transcriptions for identical text included in the plurality of medical transcriptions.

4. The method of claim 1, wherein:
 detecting the information corresponding to the trigger from the other medical transcription comprises detecting the trigger in the other medical transcription; and
 automatically inserting the text block in the position comprises substituting the text block for the trigger in the other medical transcription.

5. The method of claim 1, further comprising:
 storing the other medical transcription in a data store of medical transcriptions upon insertion of the text block.

6. The method of claim 1, wherein the trigger corresponds to at least one word, at least one phrase and/or a regular expression.

7. The method of claim 1, further comprising:
 analyzing a plurality of audio files using one or more acoustic and/or language models; and
 determining, based on the analysis, the plurality of medical transcriptions.

8. The method of claim 7, further comprising determining the other medical transcription based on analyzing of another audio file using the one or more acoustic and/or language models.

9. The method of claim 7, wherein the acoustic and/or language models are specific to a particular speaker.

10. The method of claim 1, further comprising;
 segmenting each of the medical transcriptions in the set of medical transcriptions; and
 aligning the set of medical transcriptions based on the segmentation, wherein the analysis of the set of medical transcriptions is based on the set of medical transcriptions being aligned.

11. The method of claim 1, wherein determining that the text block occurs in the plurality of medical transcriptions comprises determining that each medical transcription in the plurality of medical transcription includes a respective text portion that exhibits at least a threshold level of similarity to the text block.

12. At least one non-transitory computer-readable storage medium having encoded thereon executable instructions that, when executed by at least one processor, cause the at least one processor to carry out a method, the method comprising:
 analyzing a set of medical transcriptions to identify a text block, wherein analyzing the set of medical transcriptions comprises determining that the text block occurs in a plurality of medical transcriptions within the set of medical transcriptions;
 storing, in at least one structured datastore, a datastore record identifying the text block and an associated trigger, the trigger being an indicator causing automatic insertion of the text block within another medical transcription when the trigger is present in the other medical transcription, the at least one datastore storing a plurality of datastore records identifying a plurality of pairs of text blocks and associated triggers;

detecting, from the other medical transcription, information corresponding to the trigger;

automatically inserting the text block in a position within the other medical transcription based on the detection; and verifying modification of the other medical transcription via the insertion of the text block, wherein verification comprises determining an accuracy of the insertion of the text.

13. The at least one computer-readable storage medium of claim 12, wherein analyzing the set of medical transcriptions to identify the text block comprises analyzing the plurality of medical transcriptions for text that satisfies one or more criteria.

14. The at least one computer-readable storage medium of claim 12, wherein the method further comprises configuring a transcriber to, when the trigger is present in a medical transcription of audio regarding a patient encounter, insert the text block in the medical transcription of the audio regarding the patient encounter.

15. An apparatus comprising:

at least one processor; and at least one storage medium having encoded thereon executable instructions that, when executed by the at least one processor, cause the at least one processor to carry out a method, the method comprising:

identifying an unregistered text block, wherein identifying the unregistered text block includes analyzing a set of medical transcriptions to identify a block of text, wherein analyzing the set of medical transcriptions comprises determining that the block of text occurs in a plurality of medical transcriptions within the set of medical transcriptions, wherein identifying the unregistered text block further includes searching at least one structured datastore to determine that the block of text is unregistered;

registering the unregistered text block, including generating an alert regarding the unregistered text block and storing, in the at least one structured datastore, a datastore record identifying the block of text and an associated a trigger, the trigger being an indicator causing automatic insertion of the block of text within another medical transcription when the trigger is present in the other medical transcription, the at least one datastore storing a plurality of datastore records identifying a plurality of pairs of registered text blocks and associated triggers;

detecting, from the other medical transcription, information corresponding to the trigger;

automatically inserting the text block in a position within the other medical transcription based on the detection; and verifying modification of the other medical transcription via the insertion of the text block, wherein verification comprises determining an accuracy of the insertion of the text.

16. The apparatus of claim 15, wherein analyzing the set of medical transcriptions to identify the text block comprises analyzing the plurality of medical transcriptions for text that satisfies one or more criteria for similar text.

* * * * *